United States Patent [19]

Fedorov et al.

[11] Patent Number: 5,725,576
[45] Date of Patent: Mar. 10, 1998

[54] POLYMER MATERIAL FOR MAKING AN ELASTIC INTRAOCULAR LENS AND A LENS BASED ON SAID MATERIAL

[75] Inventors: Svyatoslav Nikolaevich Fedorov; Leonid Feodosievich Linnik, both of Moscow; Valery Mikhailovich Treushnikov; Elena Alexandrovna Viktorova, both of Nizhny Novgorod, all of Russian Federation

[73] Assignees: Mezhotraslevoi Nauchno-Tekhnichesky Komplex "Mikrokhirurgia Glaza", Moscow; Tovarischestvo S Ogranichennoi Otvetstvennostju "Svetoplastik", Nizhny Novgorod, both of Russian Federation

[21] Appl. No.: 656,693

[22] Filed: May 31, 1996

[30] Foreign Application Priority Data

Jun. 1, 1995 [RU] Russian Federation ............ 95108279

[51] Int. Cl.$^6$ ...................................................... A61F 2/16
[52] U.S. Cl. .......................... 623/6; 430/284.1; 430/300; 523/106; 351/159
[58] Field of Search ........................ 351/159; 430/284.1, 430/300; 523/106; 623/6

[56] References Cited

U.S. PATENT DOCUMENTS

| | | | |
|---|---|---|---|
| 4,110,184 | 8/1978 | Dart et al. | 430/284.1 |
| 4,166,088 | 8/1979 | Neefe | 264/1 |
| 4,206,518 | 6/1980 | Jardon et al. | 3/13 |
| 4,382,902 | 5/1983 | Feurer | 264/1.4 |
| 4,834,750 | 5/1989 | Gupta | 623/6 |
| 5,476,749 | 12/1995 | Steinmann et al. | 430/284.1 |
| 5,495,029 | 2/1996 | Steinmann et al. | 430/284.1 |

FOREIGN PATENT DOCUMENTS

| | | | |
|---|---|---|---|
| 1428368 | 10/1988 | Russian Federation . | |
| 2150938 | 7/1985 | United Kingdom | 523/106 |

OTHER PUBLICATIONS

S. N. Fyodorov et al. Ophthalmosurgery, No. 2, pp. 24–29, "Cataract Surgery", 1992.

*Primary Examiner*—Paul B. Prebilic
*Attorney, Agent, or Firm*—Jacobson, Price, Holman & Stern, PLLC

[57] ABSTRACT

The polymer material is a mixture, consisting substantially of:

oligourethanemethacrylate having the following structural formula:

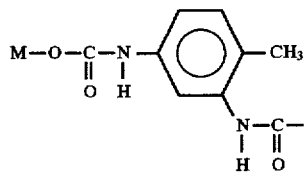
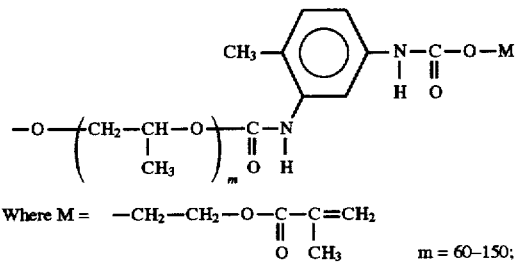

Where M = 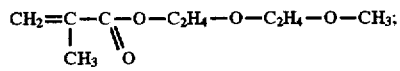 m = 60–150;

methylcarbitol methacrylate

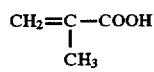

methacrylic acid $$CH_2=C-COOH$$
$$\quad\;\;|$$
$$\;\;CH_3$$

and 2,2'-dimethoxy-2-phenylacetophenone
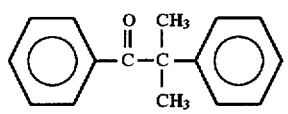
taken in ratio that ensure the ability of the mixture to light curing under the effect of UV radiation. The intraocular lens comprises an optic and a supporting portion, both made substantially of the mentioned polymer material.
4 Claims, 1 Drawing Sheet

POLYMER MATERIAL FOR MAKING AN ELASTIC INTRAOCULAR LENS AND A LENS BASED ON SAID MATERIAL

FIELD OF THE INVENTION

The present invention relates to medicine and more specifically it concerns a polymer material for making an elastic intraocular lens, such an elastic intraocular lens based on said material, and a method for making said lens; the invention can find application in opthalmology.

BACKGROUND OF THE INVENTION

At present most applicable in ophthalmology are intraocular lenses made of polymethylmethacrylate (cf. Posterior-chamber intraocular correction of traumatic cataract and aphakia, by S. N. Fyodorov et al., Opthalmosurgery No. 2, 1991, p. 5).

Intraocular lenses from polymethylmethacrylate feature good optical characteristics and low toxicity. However, said lenses are very hard and rigid and hence are likely to cause postoperative complications, i.e., injury to the surrounding eye tissues.

Known in the art presently are intraocular lenses from organosilicon polymers (silicones) (U.S. Pat. No. 1,428, 368; U.S. Pat. No. 4,206,518), from collagen copolymer (Correction of aphakia by implanting an intraocular lens from a novel biocompatible material, collagen copolymer, by S. N. Fyodorov et al., Ophthalmosurgery, No. 2, 1992, p. 24), and from a hydrogel (2-hydroxyethylmethacrylate) (Hydrogel intraocular lens in surgery of cataract, by S. N. Fyodorov et al, Ophthalmosurgery, No. 4, 1990, p. 18).

However, materials used for said intraocular lenses are featured by low internal cohesion with the resultant low strength of such a lens and its destruction when folded up. Low strength of intraocular lenses made from said materials prevents injector introduction of such lenses into patient's eye.

Moreover, all such materials are much more toxic compared with polymethylmethacrylate which makes postoperative inflammatory processes in the eye more probable.

Some prior-art elastic intraocular lenses are known to be made of spatially cross-linked acrylic rubbers (U.S. Pat. No. 4,834,750).

Intraocular lenses of said material are adequately strong and can be folded up and injected into the eye through the pupillary orifice. However, such lenses are highly reactive upon interaction with the eye tissues.

One prior-art method for making intraocular lenses by high-temperature vulcanization of a silicone polymer in a casting mold, followed by placing in a temperature-controlled cabinet (U.S. Pat. No. 1,428,368).

However, a prolonged holding of all now-existing polymers at high temperatures (200°–300° C.) results not only in their cross-linking (vulcanization) but also destruction. Polymer destruction leads to formation of low-molecular products capable of diffusing into the eye tissues, thus causing toxic effects.

In addition, only a very narrow range of materials can used for making intraocular lenses by said method, that is, such ones, wherein the shrinkage factor approximates zero. The abovesaid applies equally to methods for making lens, wherein curing of liquid metal in a casting mold occurs under the effect of light or some other radiation. Forasmuch as the shrinkage factor of an overwhelming majority of light-cured materials lies within 5 and 22%, such methods are believed as unsuitable for making lenses having acceptable optical characteristics (cf. Polymer optic materials. A collection of papers, Chernogolovka, 1989).

Known nowadays are methods for making eye contact lenses by curing a liquid material in a mold made from an optically transparent material under the effect of UV radiation (U.S. Pat. No. 4,382,902; U.S. Pat. No. 4,166,088).

It is should be noted, however, that the above-mentioned patents disclose methods for making contact lenses rather than intraocular lenses. Contact lenses are in fact convexo-concave lenses which are not featured by a considerable variation in thickness. In this connection, it is conceivable that damping devices provided in casting molds make it possible to attain adequate optical characteristics of contact lenses. As distinct from the latter, intraocular lenses are biconvex or planoconvex lenses, wherein variation in thickness is much higher than in contact lenses. Thus, none of the casting mold constructions makes it possible to produce intraocular lenses having adequate optical characteristics, using the aforesaid method.

SUMMARY OF THE INVENTION

It is an object of the present invention to provide a low-density intraocular lens.

It another object of the present invention to provide an intraocular lens capable of being folded up and of restitution of its preset shape.

It is one more object of the present invention to provide a low-toxic intraocular lens nonreactive towards the intraocular humor.

Said objects are accomplished due to the fact that a polymer material for making a methacrylate-based elastic intraocular lens, according to the invention, is essentially a mixture of components which consists substantially of:

oliguorethanemethacrylate having the following structural formula:

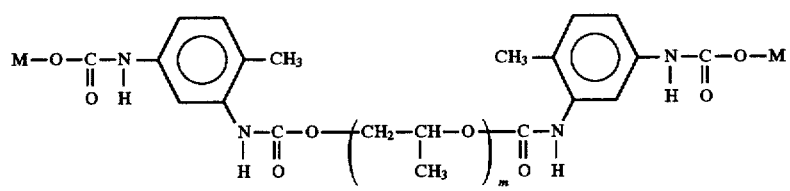

methylcarbitol methacrylate

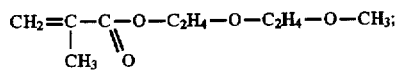

methacrylic acid

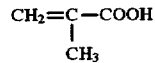

and 2,2'-dimethoxy-2-phenylacetophenone

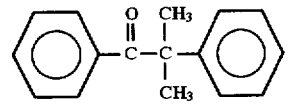

taken in ratios that ensure the ability of the mixture to light-curing under the effect of UV radiation.

It is expedient that the polymer material contains said components taken substantially in the following weight percent ratios:

| | |
|---|---|
| 2,2-dimethoxy-2-phenylacetophenone | 0.1–0.8 |
| methacrylate acid | 2–10 |
| methylcarbitol methacrylate | 10–40 |
| oligourethanemethacryalte | to make up 100% |

The foregoing objects are accomplished also due to the fact in an intraocular lens, comprising an optic and a supporting portion both made of a polymer material based on methacrylates, according to the invention, the polymer material is essentially a mixture of components which consists substantially of:

oligourethanemethacrylate having the following structural formula:

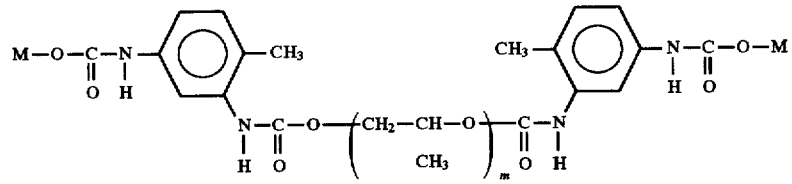

methylcarbitol methacrylate

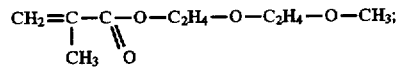

methacrylic acid

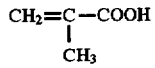

and 2,2'-dimethoxy-2-phenylacetophenone

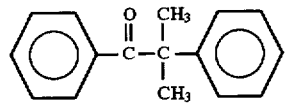

taken in ratios that ensure the ability of the mixture to lightcuring under the effect of UV radiation.

It is expedient that the polymer material contains said components taken substantially in the following weight percent ratios:

| | |
|---|---|
| 2,2-dimethoxy-2-phenylacetophenone | 0.1–0.8 |
| methacrylic acid | 2–10 |
| methylcarbitol methacrylate | 10–40 |
| oligourethanemethacrylate | to make up 100% |

The foregoing objects are accomplished also due to the fact that in a method for making an intraocular lens, consisting in irradiating, with a focused UV radiation, a liquid lightcurable polymer material placed in a casting mold which is made up of two half-molds and made of an optically transparent material, according to the invention, said liquid polymer material is essentially a mixture of components which consists substantially of:

oligourethanemethacrylate having the following structural formula:

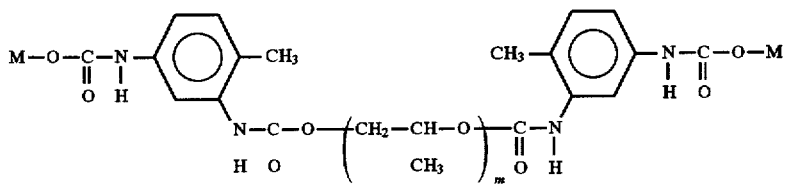

Where M = —CH₂—CH₂—O—C(=O)—C(CH₃)=CH₂    m = 60–150;

methylcarbitol methacrylate

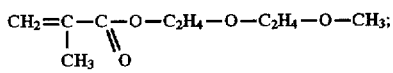

methacrylic acid $$CH_2=C(CH_3)-COOH$$

and 2,2'-dimethoxy-2-phenylacetophenone

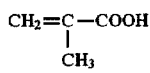

taken in ratios that ensure the ability of the mixture to light-curing under the effect of UV radiation, the half-molds of the casting mold are shaped as cylinders having optically polished end faces and being provided with recesses made on the inner surfaces of the central portion thereof, said recesses forming the optic portion of the intraocular lens after the two half-molds of the casting mold are joined together; a pattern is provided on the inner surface of one of the half-molds, comprising areas transparent to UV radiation and those opaque thereto, a negative image of said pattern corresponding to a two-dimensional image of the lens optic portion and of the supporting portion thereof; a similar pattern is provided on the inner surface of the other half-mold, a negative image of said pattern corresponding to the image of the lens optic portion alone; the casting mold is irradiated in two stages, the first one being effected by establishing a variable illumination and a variable diameter of a diffusion spot; first the radiation is focused at the mold axis, then it moves uniformly towards the edges of said openings, thus covering their entire area and hence forming the optic portion of the intraocular lens; in the second stage the mold is irradiated uniformly over its entire area, thus forming the supporting portion of the intraocular lens, whereupon the half-mold of the casting mold on which the intraocular lens has been formed, is treated to yield a finished elastic intraocular lens.

It is expedient that the polymer material contains said components taken substantially in the following weight percent ratios:

| | |
|---|---|
| 2,2-dimethoxy-2-phenylacetophenone | 0.1–0.8 |
| methacrylic acid | 2–10 |
| methylcarbitol methacrylate | 10–40 |
| oligourethanemethacrylate | to make up 100% |

In the herein-proposed polymer material, elastic intraocular lens, and a method for making said lens, the minimum values of ingredients in said compositions determines the threshold value, from the standpoint of a minimum, below which either the required elasticity and strength of the lens are unattainable or the polymerization process proceeds incompletely which results in the onset of acute reactions in the eye tissues, whereas the maximum values of the ingredients are determined by the fact that at greater values results either in an excess rigidity of the lens or in deteriorated optic characteristics thereof (that is, distorted shape, opacity, and the like).

It is reasonable that at said first stage the effect of UV radiation is applied at a uniform rate not exceeding the cure rate of the polymer material.

It is quite reasonable that treatment of the half-mold on which said intraocular lens has been formed includes development consisting in eliminating uncured polymer material from the inner end face of the half-mold, whereon the intraocular lens has been formed, and annealing said half-mold.

It is expedient that annealing includes placing the half-mold, whereon the intraocular lens has been formed, in bidistilled water at a temperature of from 40° to 60° C., and exposing said water-immersed half-mold to UV radiation for 3 to 10 minutes.

The present invention provides for producing an optically transparent elastic intraocular lens capable of folding up and restituting its preset shape.

BRIEF DESCRIPTION OF THE DRAWINGS

The foregoing and further objects of the present invention will become more evident from consideration of a detailed description of some specific exemplary embodiments thereof with reference to the appended drawings, wherein.

DETAILED DESCRIPTION OF THE INVENTION

Figure 1:
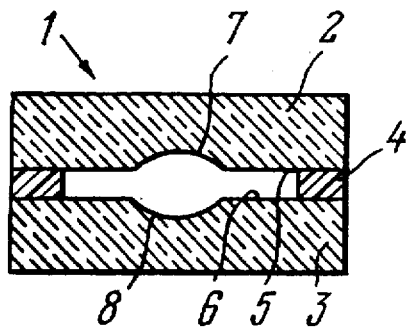
FIG. 1 is a general longitudinal sectional view of an assembled casting mold, according to the invention.

The polymer material for making an elastic intraocular lens, according to the invention, is essentially a mixture of components which consists substantially of:

oligourethanemethacrylate having the following structural formula:

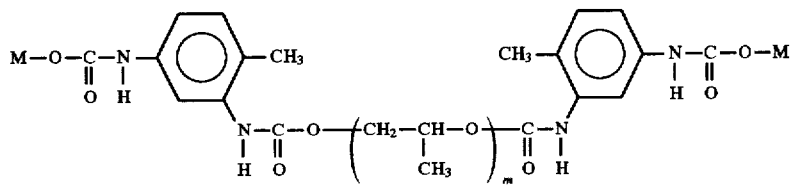

Where M = —CH$_2$—CH$_2$—O—C—C=CH$_2$
                              ‖   |
                              O  CH$_3$     m = 60–150;

methylcarbitol methacrylate

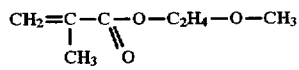

methacrylic acid

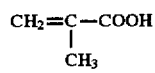

and 2,2'-dimethoxy-2-phenylacetophenone

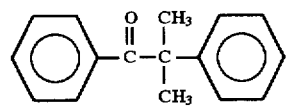

taken in ratios that ensure the ability of the mixture to light-curing under the effect of UV radiation.

It is expedient that the polymer material contains said components taken substantially in the following weight percent ratios:

| | |
|---|---|
| 2,2-dimethoxy-2-phenylacetophenone | 0.1–0.8 |
| methacrylic acid | 2–10 |
| methylcarbitol methacrylate | 10–40 |
| oligourethanemethacrylate | to make up 100% |

The proposed elastic intraocular lens based on the aforedescribed polymer material comprises an optic portion and a supporting portion the production process of both being hereinafter described in detail with reference to the accompanying drawings. The optic and supporting portions are joined together and made of a polymer material based on methacrylates. The polymer material is essentially the aforementioned mixture of components taken in the aforestated ratios.

The proposed method for making the intraocular lens, according to the invention, based on the proposed material is the subject of a detailed description given hereinbelow.

The method proposed herein is as follows.

A casting mold 1 (FIG. 1) used for making the intraocular lens, according to the invention, is built up of two half-molds 2 and 3 made from an optically transparent material, such as quartz, and an annular spacer 4 made of, e.g., sheet polytetrafluoroethylene and having a thickness equal to that of the lens supporting portion.

A casting mold 1 are shaped as cylinders having optically polished end faces being provided with recesses 7, 8 made on inner surfaces 5, 6 of the central portion thereof, said openings forming the optic portion of the proposed intraocular lens after the two half-molds 2 and 3 of the casting mold 1 have been joined together.

Figure 2:
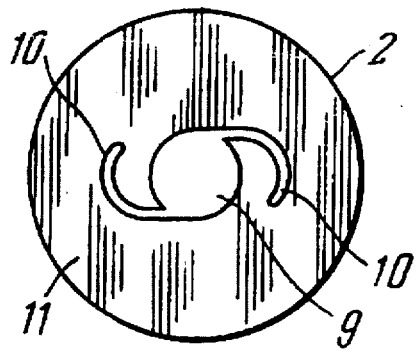
FIG. 2 is a bottom view of the inner surface of the upper half-mold of FIG. 1 (with the lower half-mold out of position)

A pattern is provided on the inner surface 5 (FIG. 1) of the upper half-mold 2 of the casting mold 1, comprising areas 9 (FIG. 2) and 10 transparent to UV radiation and areas 11 opaque to said radiation and made of, e.g., chromiumm a negative image of said pattern corresponding respectively to a two-dimensional image of the lens optic portion and of the supporting portion thereof as shown in FIG. 2. A similar pattern is provided on the inner surface 6 (FIG. 1) of the lower half-mold 3 of the casting mold 1, a negative image of said pattern corresponding to the image of the lens optic portion alone.

Figure 4:
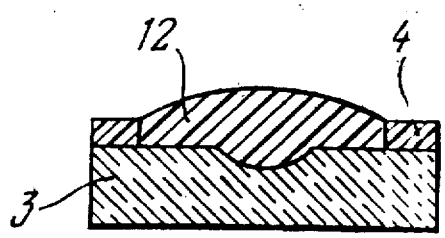
FIG. 4 a longitudinal sectional view of the lower half-mold of the casting mold of FIG. 1 after filling the polymer material therein.
Figure 5:
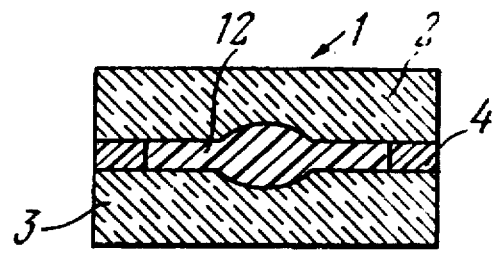
FIG. 5 is a general longitudinal sectional view of an assembled casting mold with the polymer material filled therein.
Figure 3:
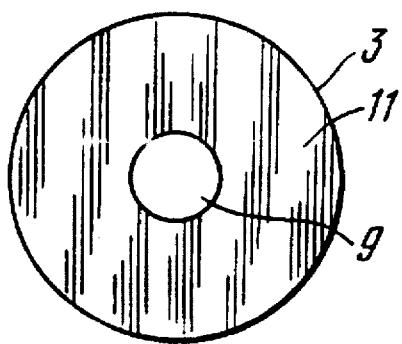
FIG. 3 is a top view of the inner surface of the lower half-mold of FIG. 1 (with the upper half-mold out of position)

The annular spacer 4 is set on the lower half-mold 3 (FIG. 4) of the casting mold 1, whereupon a liquid polymer material 12 is filled in said lower half-mold 3 to form the upper meniscus, the upper half-mold 2 (FIG. 5) is put on the lower one, the centers of the half-molds 2 and 3 of the casting mold 1 are brought in register (on the axis of the mold 1) along the two coordinates in the plane thereof, and both of the half-molds are tightly pressed against each other. The polymer material 12 is essentially the aforementioned mixture of the components taken in the aforestated limit values.

Figure 6:
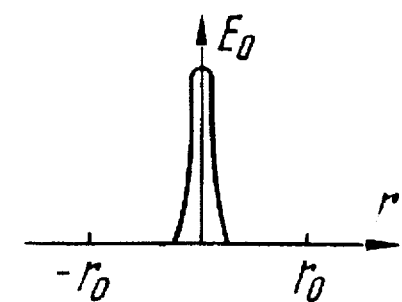
FIG. 6 represents a distribution curve of light intensity $E_o$ at the initial instant of exposure, where $r_o$ is the radius of the optic portion of the proposed intraocular lens made by the method, according to the invention.
Figure 7:
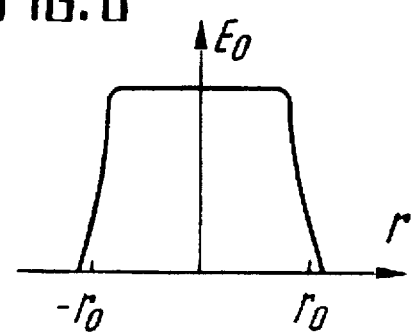
FIG. 7 represents a distribution curve of light intensity $E_o$ at the instant of time corresponding to a completely illuminated optic portion of the proposed intraocular lens made by the method, according to the invention.

Then the mold is exposed to UV radiation with a wavelength of from 320 to 380 nm in two stages. At the first stage of exposure there is established a variable illumination with a variable diameter of a diffusion spot. First the UV radiation from an external source (not shown) is focused at the center of the mold 1 (at the mold axis), whereupon the radius of the area being illuminated is increased at a uniform rate not exceeding the cure rate of the material 12 until said radius becomes equal to the radius of the optic portion of the proposed intraocular lens. Illumination distribution lengthwide the diameter of the lens optic portion at the initial instant of time should be such as shown in FIG. 6, that at the terminal stage of exposure, as shown in FIG. 7. Illumination of the mold 1 (FIG. 5) during its irradiation is varied with the aid of an extensively known exposure unit (not shown), consisting of a light source (mercury-quartz lamp), a diaphragm, an optic system allowing for projecting the diaphragm open portion onto the surface of the casting mold 1, and a device enabling one to open the diaphragm at a preset rate. The rate of light spot expansion is so selected that complete curing of the liquid polymer material 12 occurs as soon as the light spot reaches the boundary of the lens optic portion.

At the second stage of exposure the casting mold 1 is irradiated over its entire area from a light source (not shown) that provides for a uniform illumination of the whole area of the casting mold 1. An optimum exposure time is selected empirically so that, after developing the proposed intraocular lens, the linear dimensions of the lens supporting portion are to correspond to the dimensions shown in FIG. 2.

Once the irradiation of the casting mold 1 has been completed, the half-molds 2 and 3 thereof are disjoined. The intraocular lens remains in one of the half-molds of the mold 1, as well as the remainder of the uncured liquid polymer material 12. Then the lens is carefully developed in an appropriate solvent, such as isopropyl alcohol, whereupon the lens is additionally irradiated, after having been immersed in bidistilled water without being separated from the mold 1, with UV radiation for 3–10 minutes at 40°–60° C.

Given below are some specific examples of practical embodiment of the proposed method for making an intraocular lens, according to the invention, based on the proposed polymer material.

EXAMPLE 1

Added successively to a reaction flask provided with a stirrer are 78.19 g of oligourethanemethacrylate having the number of the groups

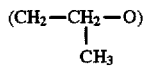

m=80, 13.7 g of methylcarbitol methacrylate, 7.77 g of methacrylic acid, and 0.34 g of 2,2-dimethoxy-2-phenylacetophenone.

The resultant mixture is stirred at room temperature for 40 min till a complete dissolution of 2,2-dimethoxy-2-phenylacetophenone.

Once stirred the composition is passed through a filter and pumped out with the aid of a vacuum at a residual pressure of 0.5–1 mm Hg until gas evolution ceases completely.

The pumped-out composition is used for making the proposed intraocular lens.

The aforesaid lens is produced in the quartz casting molds 1 (FIG. 1), composed of the two half-molds 2, 3 whose technical characteristics are specified in Table 1 that follows the Examples. The lower half-molds 3 of the molds 1 (mold Nos 1, 2, 3, 4 in Table 1) are arranged horizontally so that the recess 8 for the lens optic portion is at the top. The ring-shaped spacers 4 made of sheet polytetrafluoroethylene 150 μm thick, are put onto the surfaces 6. Then the preprepared composition is inserted, using a 200-μl microdispenser (not shown), into the recess 8 (FIG. 4) of the half-molds 3 of the casting molds 1 (FIG. 1). Then the upper half-molds 2 (FIG. 5) of the casting molds 1 are put onto the lower ones and are so pressed thereagainst that the composition fills completely the entire space between the two half-molds 2 and 3 of the casting molds 1 confined to the spacer 4. The casting molds 1 are filled with said composition at room temperature in a yellow light and a dustfree atmosphere.

Each of the casting molds 1 is placed under an extensively known microscope, whereupon one tries, at a X12 magnification, to bring the edge of the optic portion of the upper half-mold 2 in coincidence with the edge of the optic portion of the lower half-mold 3 of the casting mild 1 by moving the lower half-mold 3 with respect to the upper half-mold. Then the matched up casting mold 1 is tightly pressed and fixed in this position.

Next the casting mold 1 is placed in the exposure unit (not shown), comprising a light source (mercury-quartz lamp), a diaphragm, an optic system adapted to project the open diaphragm portion onto the surface of the casting mold 1, and a device adapted to open the diaphragm at a preset rate. The casting mold 1 is so positioned in the exposure unit that an incident light ray passes along the main axis of the optic portion of the casting mold 1, and the image of the diaphragm is generated in a plane parting the half-molds 2 and 3 from each other. The diaphragm is in a closed state before starting the exposure procedure. Then the rate of the diaphragm opening is set, corresponding to an increase in the radius of the illuminated area of the optic portion by 3.5 mm for 7 min, whereupon the first stage of the exposure procedure is conducted, at which the optical portion of the proposed intraocular lens is formed.

Then the casting mold 1 is placed under another exposure unit (not shown), comprising a light source (mercury-quartz lamp) and a collimator, and a second exposure stage is carried out. An optimum exposure time is selected empirically so that after developing the proposed intraocular lens, the linear dimensions of the lens supporting portion are to correspond to the dimensions shown in FIG. 2. With an intensity of radiation incident upon the surface of the casting mold 1, equal to 440 W/sq.m. an optimum exposure time is 1 min 30 s. At the second stage of the exposure procedure the supporting (haptic) portion of the intraocular lens is formed.

Once irradiated the casting mold 1 is disassembled by disjoining the half-mold 2 from the half-mold 3 and removing the limiting spacer 4. All subsequent operations deal with that half-mold of the casting mold 1 on which the intraocular lens has been formed.

The half-mold carrying the thus-formed intraocular lens is placed in a developing unit (not shown), comprising a 200-ml developing dish, a developer circulating pump, and an injector provided in the dish lid. The half-mold carrying the lens is placed in the dish, a developer (isopropyl alcohol) is filled therein, the dish is closed with the lid, and the pump is turned on, the development time being 2 min. It is during the development that the unpolymerized portion of the light-curable material is eliminated, which has been under the UV-opaque areas 11 (FIG. 2) of the pattern made on the inner surface 5 (FIG. 5) of the upper half-mold 2 of the casting mold 1.

The development over, the half-mold carrying the lens is dried in a stream of warm dustfree air for 5 min, then placed in a 100-ml dish filled with bidistilled water preheated to 40°–60° C. The dish is placed in an exposure unit (not shown), comprising a light source (mercury-quarts lamp), and an annealing stage is performed, consisting in exposing the intraocular lens to an additional UV-radiation. With an intensity of radiation incident upon the lens surface equal to 440 W/sq.m, the exposure time is 10 min. After having been exposed to an additional irradiation, the lens is dried of water and separated from the half-mold.

The finished product appears as optically transparent elastic intraocular lenses whose characteristics are set forth in Table 2 that follows Table 1.

EXAMPLE 2

The composition is prepared as in Example 1, the amount of the components being as follows (g):

| | |
|---|---|
| oligourethanemethacrylate having the number of the groups | 87.9, |
| $(CH_2-CH_2-O)\ m = 60$<br>$\qquad\ \|$<br>$\qquad CH_3$ | |
| methylcarbitol methacrylate | 10, |
| methacrylic acid | 2, |
| 2,2-dimethoxy-2-phenylacetophenone | 0.1. |

The intraocular lens is produced as in Example 1.
The lens characteristics are contained in Table 2.

EXAMPLE 3

The composition is prepared as in Example 1, the amount of the components being as follows (g);

| | |
|---|---|
| oligourethanemethacrylate having the number of the groups | 49.2, |
| $(CH_2-CH_2-O)\ m = 150$<br>$\qquad\ \|$<br>$\qquad CH_3$ | |
| methylcarbitol methacrylate | 40, |
| methacrylic acid | 10, |
| 2,2-dimethoxy-2-phenylacetophenone | 0.8. |

The intraocular lens is produced as in Example 1.
The lens characteristics are contained in Table 2.

EXAMPLE 4

The composition is prepared as in Example 1, the amount of the components being as follows (g);

| | |
|---|---|
| oligourethanemethacrylate having the number of the groups | 93.5, |
| $(CH_2-CH_2-O)\ m = 50$<br>$\qquad\ \|$<br>$\qquad CH_3$ | |
| methylcarbitol methacrylate | 5, |
| methacrylic acid | 1, |
| 2,2-dimethoxy-2-phenylacetophenone | 0.5. |

The intraocular lens is produced as in Example 1.
The lens characteristics are contained in Table 2.

EXAMPLE 5

The composition is prepared as in Example 1, the amount of the components being as follows (g);

| | |
|---|---|
| oligourethanemethacrylate having the number of the groups | 23, |
| $(CH_2-CH_2-O)\ m = 170$<br>$\qquad\ \|$<br>$\qquad CH_3$ | |
| methylcarbitol methacrylate | 60 |
| methacrylic acid | 15 |
| 2,2-dimethoxy-2-phenylacetophenone | 2 |

The intraocular lens is produced as in Example 1.
The lens characteristics are contained in Table 2.

EXAMPLE 6

The composition is prepared as in Example 1. The intraocular lens is produced as in Example 1, but the rate of the diaphragm opening is set to correspond to an increase in the radius of the illuminated area of optic portion by 3.5 mm for 4 min, whereupon a first stage of the exposure procedure is carried out.

The lens characteristics are contained in Table 2.

EXAMPLE 7

The composition is prepared as in Example 1. The intraocular lens is produced as in Example 1, but the rate of the diaphragm opening is set to correspond to an increase in the radius of the illuminated area of optic portion by 3.5 mm for 10 min, whereupon a first stage of the exposure procedure is carried out.

The lens characteristics are contained in Table 2.

EXAMPLE 8

The composition is prepared with the amount of the components as in Example 1, but the annealing stage is carried out at a bidistilled water temperature of 20° C.

The lens characteristics are contained in Table 2.

EXAMPLE 9

The composition is prepared with the amount of the components as in Example 1, but the annealing stage is carried out at a bidistilled water temperature of 90° C.

The lens characteristics are contained in Table 2.

TABLE 1

| Mold No. | Radius of curvature of recess, mm | Diameter of recess, mm |
|---|---|---|
| 1 | 18 | 5.5 |
| 2 | 16 | 5.5 |
| 3 | 14.4 | 5.5 |
| 4 | 13.6 | 5.5 |

TABLE 2

| Light-curable material as per Example No. 1 | Mold No. in Table 1 2 | Refractive index 3 | Lens refraction, diopters 4 | Density g/cu · cm 5 | Resolution, lines/mm 6 |
|---|---|---|---|---|---|
| 1 | 1 | 1.4795 | 16 | 1.12 | 200 |
|   | 2 | 1.4795 | 18 | 1.12 | 200 |
|   | 3 | 1.4795 | 20 | 1.12 | 200 |
|   | 4 | 1.4795 | 21 | 1.12 | 200 |
| 2 | 1 | 1.4795 | 16 | 1.12 | 200 |
|   | 2 | 1.4795 | 18 | 1.12 | 200 |
|   | 3 | 1.4795 | 20 | 1.12 | 200 |
|   | 4 | 1.4795 | 21 | 1.12 | 200 |
| 3 | 1 | 1.4795 | 16 | 1.12 | 200 |
|   | 2 | 1.4795 | 18 | 1.12 | 200 |
|   | 3 | 1.4795 | 20 | 1.12 | 200 |
|   | 4 | 1.4795 | 21 | 1.12 | 200 |
| 4 | 1 | 1.4705 | 14.9 | 1.09 | 180 |
|   | 2 | 1.4706 | 16.8 | 1.10 | 180 |
|   | 3 | 1.4705 | 18.6 | 1.09 | 180 |
|   | 4 | 1.4705 | 19.7 | 1.09 | 180 |
| 5 | 1 | 1.4761 | 15.6 | 1.10 | 180 |
|   | 2 | 1.4762 | 17.5 | 1.11 | 180 |
|   | 3 | 1.4761 | 19.5 | 1.10 | 180 |
| 6 | 1 | 1.4750 | 15.4 | 1.095 | 120 |
|   | 3 | 1.4751 | 19.3 | 1.095 | 120 |
|   | 4 | 1.4750 | 20.4 | 1.095 | 120 |
| 7 | 1 | 1.4795 | 16 | 1.12 | 200 |
|   | 2 | 1.4795 | 18 | 1.12 | 200 |

TABLE 2-continued

| Light-curable material as per Example No. 1 | Mold No. in Table 1 2 | Refractive index 3 | Lens refraction, diopters 4 | Density g/cu · cm 5 | Resolution, lines/mm 6 |
|---|---|---|---|---|---|
|  | 3 | 1.4795 | 20 | 1.12 | 200 |
|  | 4 | 1.4795 | 21 | 1.12 | 200 |
| 8 | 1 | 1.4785 | 15.8 | 1.115 | 190 |
|  | 2 | 1.4785 | 17.8 | 1.115 | 190 |
|  | 3 | 1.4785 | 19.8 | 1.115 | 190 |
|  | 4 | 1.4785 | 20.7 | 1.115 | 190 |
| 9 | 1 | 1.4775 | 15.7 | 1.10 | 190 |
|  | 2 | 1.4775 | 17.6 | 1.10 | 190 |
|  | 3 | 1.4775 | 19.6 | 1.10 | 190 |
|  | 4 | 1.4775 | 20.7 | 1.10 | 190 |

Notes

1. The refractive index of the light-curable material is found from the formula:

$$n = 1 + R/2F,$$

where

F is the lens focal length,

R is the radius of curvature of the anterior and posterior lens surfaces ($R1=R2=R$);

2. The lens focal length is found from the formula $F=a$, where a is the distance from the image of an object to the main lens optic plane with an infinitely remote light source;

3. The refraction value is found from the formula:

$$D = 2\Delta n/R,$$

where $\Delta n$ is a difference between the refractive index of the light-curable material the lens is made of and that of the aqueous humor of the eye ($N=1.336$);

4. The lens density is determined using the standard procedure for finding the density of polymer materials;

5. Resolution is determined by a line-type mire placed in the lens focal plane.

It ensues from Table 2 that in those Examples (Nos. 1, 2, 3, and 7) wherein the ingredients of the light-curable composition and the method for making the lens comply with the Claims for Patent, the resultant intraocular lenses feature the maximum values of refractive index, density, and resolution. As studies have demonstrated, in such intraocular lenses the polymerization process is fully completed so that such lenses are quite untoxic for patients. On the other hand, any deviation as to the formulation or the method for making the lens (as in Example 4, 5, 6, 8 and 9) results in a reduced refractive index, density, and resolution of the intraocular lens and hence in appearance of toxicity.

In describing the herein-considered embodiments of the present invention specific narrow terminology is resorted to for the sake of clarity. However, the invention is by no way restricted to the conventional terms, and it is to be understood that each such term covers all equivalent elements functioning in a similar way and used for accomplishing similar purposes.

Although the present invention has been described in connection with a preferred embodiment thereof, it should be understood that various modifications and changes may take place without departing from the spirit and scope of the invention, as will be readily understood by those skilled in the art.

All such modifications and changes will be considered to remain within the limits of the spirit and scope of the invention as defined by the claims appended thereto.

We claim:

1. A polymer material for making an elastic intraocular lens, which is a mixture of components consisting essentially of:

oligourethanemethacrylate having the following structural formula:

$$M-O-\underset{\underset{O}{\|}}{C}-\underset{\underset{H}{|}}{N}-\underset{}{\bigcirc}-CH_3$$

(with additional connections to phenyl groups and)

Where $M = -CH_2-CH_2-O-\underset{\underset{O}{\|}}{C}-\underset{\underset{CH_3}{|}}{C}=CH_2$ $m = 60-150;$ methylcarbitol methacrylate $$CH_2=\underset{\underset{CH_3}{|}}{C}-\underset{\underset{O}{\|}}{C}-O-C_2H_4-O-C_2H_4-O-CH_3;$$

methacrylic acid $$CH_2=\underset{\underset{CH_3}{|}}{C}-COOH$$

and 2,2'-dimethoxy-2-phenylacetophenone $$\bigcirc-\underset{\underset{O}{\|}}{C}-\underset{\underset{CH_3}{\overset{CH_3}{|}}}{C}-\bigcirc$$

taken in ratios that ensure the ability of the mixture to cure under the effect of UV radiation.

2. A polymer material according to claim 1, comprising substantially said components taken in the following weight percent ratios:

| 2,2-dimethoxy-2-phenylacetophenone | 0.1–0.8 |
|---|---|
| methacrylic acid | 2–10 |
| methylcarbitol methacrylate | 10–40 |
| oligourethanemethacrylate | to make up 100%. |

3. An elastic intraocular lens, comprising:

an optical portion made of a polymer material based on methacrylates;

a supporting portion made of said polymer material based on methacrylates and connected to said optic portion;

said polymer material said optic portion and said supporting portion are made of, being a mixture of components consisting essentially of:

oligourethanemethacrylate having the following structural formula:

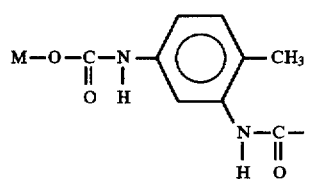

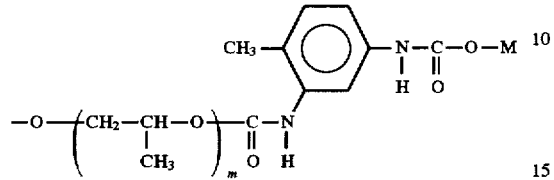

Where M = —CH$_2$—CH$_2$—O—C(=O)—C(CH$_3$)=CH$_2$ ; m = 60–150;

methylcarbitol methacrylate

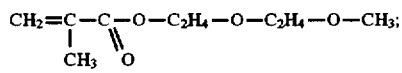

methacrylic acid

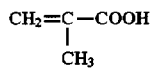

and 2.2'-dimethoxy-2-phenylacetophenone

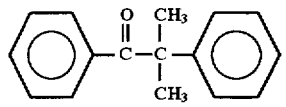

taken in ratios that ensure the ability of the mixture to cure under the effect of UV radiation.

4. An elastic intraocular lens according to claim 3, said polymer material thereof comprises substantially said components taken in the following weight percent ratios:

| | |
|---|---|
| 2.2-dimethoxy-2-phenylacetophenone | 0.1–0.8 |
| methacrylic acid | 2–10 |
| methylcarbitol methacrylate | 10–40 |
| oligourethanemethacrylate | to make up 100%. |

\* \* \* \* \*